US010822298B2

(12) United States Patent
Tanikawa et al.

(10) Patent No.: US 10,822,298 B2
(45) Date of Patent: Nov. 3, 2020

(54) (METH)ACRYLIC MONOMER AND METHOD FOR PRODUCING SAME

(71) Applicant: OSAKA ORGANIC CHEMICAL INDUSTRY LTD., Osaka (JP)

(72) Inventors: Naoko Tanikawa, Hakusan (JP); Toru Sugiue, Hakusan (JP); Naoki Shima, Hakusan (JP)

(73) Assignee: OSAKA ORGANIC CHEMICAL INDUSTRY LTD., Osaka (JP)

( * ) Notice: Subject to any disclaimer, the term of this patent is extended or adjusted under 35 U.S.C. 154(b) by 0 days.

(21) Appl. No.: 16/339,584

(22) PCT Filed: Oct. 4, 2017

(86) PCT No.: PCT/JP2017/036109
§ 371 (c)(1),
(2) Date: Apr. 4, 2019

(87) PCT Pub. No.: WO2018/066594
PCT Pub. Date: Apr. 12, 2018

(65) Prior Publication Data
US 2020/0039916 A1    Feb. 6, 2020

(30) Foreign Application Priority Data
Oct. 5, 2016  (JP) ................. 2016-197289

(51) Int. Cl.
*C07C 69/54* (2006.01)
*C07C 43/13* (2006.01)
*C07C 67/14* (2006.01)

(52) U.S. Cl.
CPC .............. *C07C 69/54* (2013.01); *C07C 43/13* (2013.01); *C07C 43/135* (2013.01); *C07C 67/14* (2013.01); *C07C 2601/08* (2017.05)

(58) Field of Classification Search
CPC ..... C07C 69/54; C07C 2601/08; C07C 43/13; C07C 43/135; C07C 67/14
See application file for complete search history.

(56) References Cited

U.S. PATENT DOCUMENTS 6,013,416 A    1/2000  Nozaki
2017/0168394 A1  6/2017  Goto

FOREIGN PATENT DOCUMENTS

| JP | H0973173 A | 3/1997 |
| JP | H0990637 A | 4/1997 |
| JP | H10161313 A | 6/1998 |
| JP | 2009-175757 A | 8/2009 |
| JP | 2009-244395 A | 10/2009 |
| JP | 2015-169843 A | 9/2015 |
| JP | 2016-108553 A | 6/2016 |
| WO | WO 2013/042694 A1 | 3/2013 |
| WO | WO 2016/035585 A1 | 3/2016 |
| WO | WO2016/035585 | * 10/2016 |

OTHER PUBLICATIONS

International Search Report & Written Opinion, dated Nov. 14, 2017, in International Application No. PCT/JP2017/036109.
International Preliminary Report on Patentability, dated Apr. 9, 2019, in International Application No. PCT/JP2017/036109.

* cited by examiner

*Primary Examiner* — Yevgeny Valenrod
*Assistant Examiner* — Blaine G Doletski
(74) *Attorney, Agent, or Firm* — Knobbe, Martens, Olson & Bear, LLP

(57) ABSTRACT

A (meth)acrylic monomer is represented by general formula (1) (wherein $R^1$ represents a hydrogen atom or a methyl group; $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom). The (meth)acrylic monomer has a property of high acid degradability and can be removed by the action of an acid.

7 Claims, 4 Drawing Sheets

(METH)ACRYLIC MONOMER AND METHOD FOR PRODUCING SAME

PRIORITY AND CROSS REFERENCE TO RELATED APPLICATIONS

This application is the U.S. National Phase Application under 35 U.S.C. § 371 of International Application No. PCT/JP2017/036109, filed Oct. 4, 2017, designating the U.S. and published as WO 2018/066594 A1 on Apr. 12, 2018, which claims the benefit of Japanese Application No. JP 2016-197289, filed Oct. 5, 2016. Any and all applications for which a foreign or a domestic priority is claimed is/are identified in the Application Data Sheet filed herewith and is/are hereby incorporated by reference in their entireties under 37 C.F.R. § 1.57.

TECHNICAL FIELD

The present invention relates to a (meth)acrylic monomer, and a method for producing the (meth)acrylic monomer.

BACKGROUND ART

In general, as chemically amplifying resist materials, out of resist materials, the so-called alkali-soluble resins are used, which are resins having an easy solubility in alkaline developing solution.

In the alkali-soluble resins, for constituent units in each of the resins, a (meth)acrylic monomer containing a tertiary cycloalkyl group and having eliminability with acid (acid-degradability) is used to heighten the resin in solubility in alkaline developing solution (Patent Documents 1 to 6).

REFERENCES

Patent Documents

Patent Document 1: JP-A-9-73173
Patent Document 2: JP-A-9-90637
Patent Document 3: JP-A-10-161313
Patent Document 4: JP-A-2009-175757
Patent Document 5: JP-A-2009-244395
Patent Document 6: WO 2016/035585

SUMMARY

In the market, resist-patterning, which makes use of resist materials, tends to be made into finer patterning. Thus, resist materials containing an alkali-soluble resin are required to have a higher resolution and a higher sensitivity. Accordingly, as a monomer for constituent units of the resin, a (meth)acrylic monomer having a higher eliminability with acid (high acid-degradability) is desired than the respective tertiary-cycloalkyl-group-containing (meth)acrylic monomers disclosed in Patent Documents 1 to 6 described above.

In the light of the actual situation, the present invention has been made, and provides a (meth)acrylic monomer having a high eliminability with acid (high acid-degradability).

The present invention relates to a (meth)acrylic monomer represented by the following general formula (1):

[Formula 1]

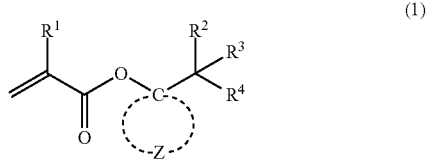

(1)

wherein $R^1$ represents a hydrogen atom or a methyl group; $R^2$ to $R^4$ independently represent $-CH_3$ or $-CH_2-O-R^5$, wherein at least one of $R^2$ to $R^4$ represents $-CH_2-O-R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

The present invention also relates to a compound represented by the following general formula (2):

[Formula 2]

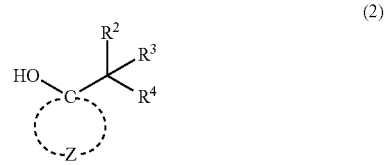

(2)

wherein $R^2$ to $R^4$ independently represent $-CH_3$ or $-CH_2-O-R^5$, wherein at least one of $R^2$ to $R^4$ represents $-CH_2-O-R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

Furthermore, the present invention relates to a method for producing the above-defined (meth)acrylic monomer that includes a step of causing (meth)acrylic acid chloride to react with the compound represented by the general formula (2).

It is presumed that the (meth)acrylic monomer of the present invention has a tertiary cycloalkyl group, and has a t-butyl group at a terminal of its alkoxy group having 1 to 4 carbon atoms, thus, a cation yielded after the methacrylic group is eliminated is made more stable, so that this monomer has a high eliminability with acid (high acid-degradability). Moreover, it is presumed that: the number of the carbon atoms in the tertiary cycloalkyl is from 3 to 10; thus, electrons therein are delocalized to make the cation more stable, so that this monomer has a high eliminability with acid (high acid-degradability).

Accordingly, the (meth)acrylic monomer of the invention is useful as an alkali-soluble resin contained in a resist material, or as a monomer for constituent units of a highly functional polymer such as a stimulation-responsive resin.

Additionally, the method of the present invention for producing a (meth)acrylic monomer can provide the (meth)acrylic monomer easily and simply.

DETAILED DESCRIPTION

<(Meth)Acrylic Monomer>

Figure 1:
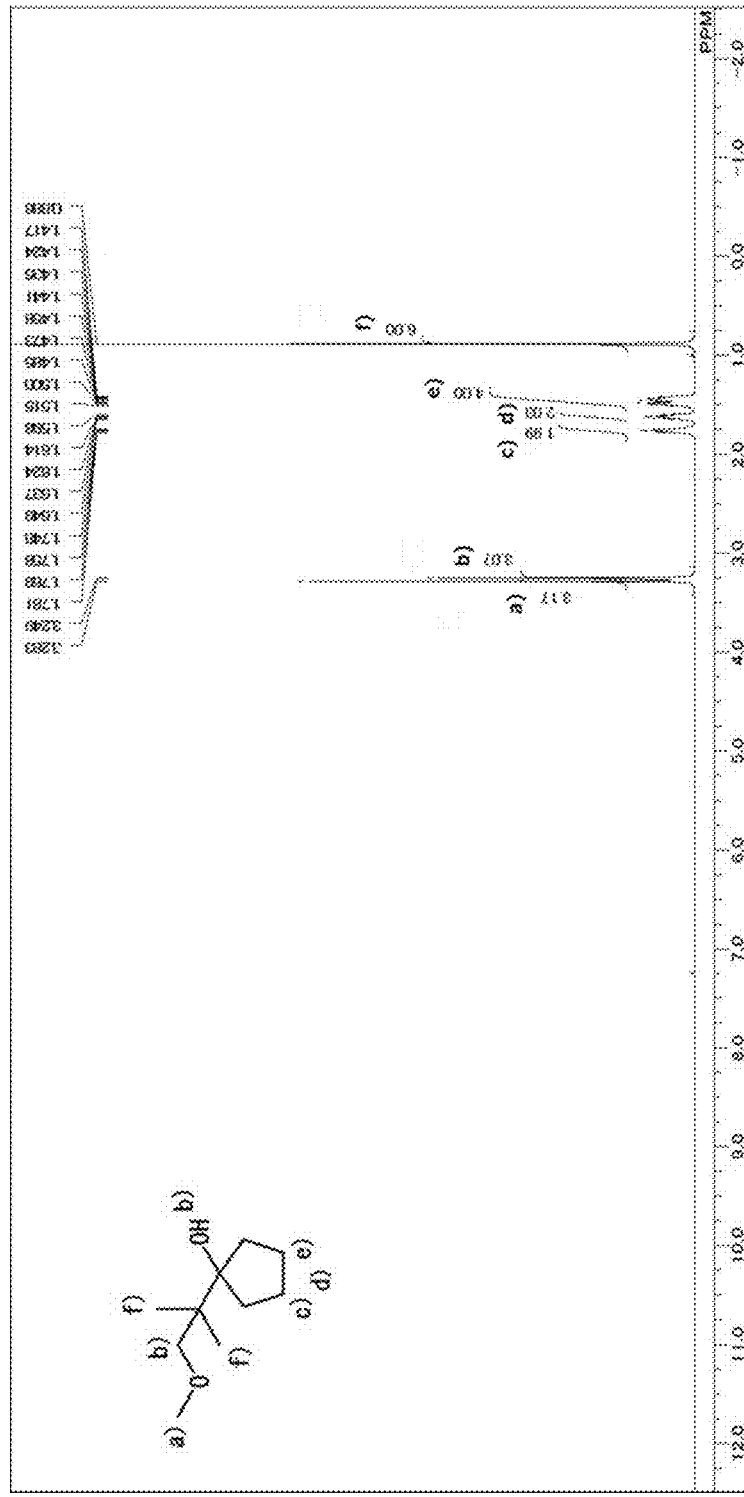
FIG. 1 is an NMR spectrum of 1-(2-methoxy-1,1-dimethyl-ethyl)-cyclopentanol represented by a general formula (6) and yielded in Example 1.

The (meth)acrylic monomer of the present invention is represented by the following general formula (1):

[Formula 3]

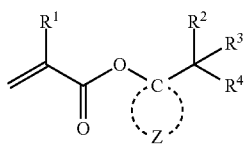

(1)

wherein $R^1$ represents a hydrogen atom or a methyl group; $R^2$ to $R^4$ independently represent $—CH_3$ or $—CH_2—O—R^5$, wherein at least one of $R^2$ to $R^4$ represents $—CH_2—O—R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

In the general formula (1), $R^2$ to $R^4$ independently represent $—CH_3$ or $—CH_2—O—R^5$ and further at least one of $R^2$ to $R^4$ represents $—CH_2—O—R^5$. About $R^2$ to $R^4$, one or two of $R^2$ to $R^4$ are (each) preferably $—CH_2—O—R^5$ from the viewpoint of giving a high eliminability with acid (high acid-degradability) to the tertiary cyclo-ester group.

In the general formula (1), $R^5$ is an alkyl group having 1 to 4 carbon atoms, and this alkyl group may be a linear or a branched chain. $R^5$ is preferably a methyl, ethyl or butyl group, and is preferably a methyl group from the viewpoint of giving a high eliminability with acid (high acid-degradability) to the tertiary cyclo-ester group.

In the general formula (1), Z represents multiple atoms necessary for the formation of an alicyclic hydrocarbon group having 3 to 10 carbon atoms in conjunction with a carbon atom. The carbon atom denotes "C" written in the general formula (1). The carbon atom in each of the general formula (2), and a general formula (5), which will be described later, has the same meaning.

The alicyclic hydrocarbon group is, for example, a monocyclic alicyclic hydrocarbon group or monocyclic alicyclic hydrocarbon group having a substituent, a condensed alicyclic hydrocarbon group or condensed alicyclic hydrocarbon group having a substituent, an adamantyl group or adamantyl group having a substituent, a dicyclopentanyl group or dicyclopentanyl group having a substituent, or an isobornyl group or isobornyl group having a substituent. The alicyclic hydrocarbon group is preferably a monocyclic alicyclic hydrocarbon group or monocyclic alicyclic hydrocarbon group having a substituent, or an adamantyl group or adamantyl group having a substituent from the viewpoint that the compound has a high eliminability with acid (high acid-degradability).

The monocyclic alicyclic hydrocarbon group having a substituent denotes a monocyclic alicyclic hydrocarbon group in which any hydrogen atom thereof is substituted with a substituent such as a methyl, ethyl, propyl, isopropyl, butyl, t-butyl, hydroxyl, carboxyl or nitrile group, or a halogen. The same matter is applicable to the condensed alicyclic hydrocarbon group having a substituent, the adamantyl group having a substituent, the dicyclopentanyl group having a substituent, and the isobornyl group having a substituent.

Examples of the monocyclic alicyclic hydrocarbon group include cyclopropane, cyclobutane, cyclopentane, cyclohexane, cycloheptane, cyclooctane, cyclononane and cyclodecane. Out of these compounds, preferred are cyclopentane, cyclohexane, cycloheptane, and cyclooctane since these compounds have a high eliminability with acid (high acid-degradability).

Examples of the condensed alicyclic hydrocarbon group include bicycloalkanes such as decahydronaphthalene, and spiro rings such as spiro[4,4]nonane.

<Method for Producing (Meth)Acrylic Monomer>

The method of the present invention for producing a (meth)acrylic monomer represented by the general formula (1) is not particularly limited, and is, for example, a producing method including a step of causing (meth)acrylic acid chloride to react with a compound represented by the general formula (2):

[Formula 4]

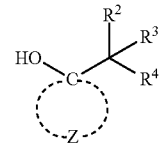

(2)

wherein $R^2$ to $R^4$ independently represent $—CH_3$ or $—CH_2—O—R^5$, wherein at least one of $R^2$ to $R^4$ represents $—CH_2—O—R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom (producing method 1).

The producing method 1 is performed preferably under an ordinary pressure, and under a nitrogen gas flow or under a nitrogen atmosphere.

In the producing method 1, (meth)acrylic acid chloride is caused to react in an amount that is preferably 0.9 moles or more, more preferably 1 mole or more per mole of the compound represented by the general formula (2), and that is preferably 10 moles or less, more preferably 9 moles or less, even more preferably 8 moles or less per mole of the same to heighten the yield of the target substance.

The reaction temperature in the producing method 1 is preferably 0° C. or higher, more preferably 10° C. or higher, and is preferably 60° C. or lower, more preferably 50° C. or lower to heighten the yield of the target substance.

The reaction period in the producing method 1 is varied in accordance with the raw materials, the reaction temperature and others. Thus, the period cannot be decided without reservation. Usually, the period is preferably 2 hours or longer, more preferably 4 hours or longer, and is preferably 48 hours or shorter, more preferably 24 hours or shorter to heighten the yield of the target substance.

In the producing method 1, an organic solvent is preferably used. The organic solvent is not particularly limited, and is preferably an inert organic solvent in the reaction system. Examples of the organic solvent include nonpolar compounds such as hexane and toluene; and polar compounds such as acetone and acetonitrile. Such organic solvents may be used singly or in any combination of two or more thereof.

In the producing method 1, the use amount of the organic solvent(s) is not particularly limited, and is usually from about 1 to 100 parts by weight for 100 parts by weight of the total of the raw materials.

In the producing method 1, a basic compound is preferably used to neutralize hydrogen chloride produced as a byproduct to heighten the yield of the target substance. Examples of the basic compound include triethylamine, pyridine, N,N-dimethyl-4-aminopyridine, 1,4-diazabicyclo[2.2.2]octane, and diazabicycloundecene. Such basic compounds may be used singly or in any combination of two or more thereof.

The basic compound(s) is/are used in an amount that is preferably 3 moles or less, more preferably 2 moles or less, even more preferably 1.4 moles or less per mole of (meth)acrylic acid chloride.

The producing method 1 is performed preferably in the presence of a polymerization inhibitor (polymerization preventer) to restrain the polymerization of (meth)acrylic acid chloride or the (meth)acrylic monomer.

Examples of the polymerization inhibitor include 4-hydroxy-2,2,6,6-tetramethylpiperidine-N-oxyl, 4-acetamino-2,2,6,6-tetramethylpiperidine-N-oxyl, 4-benzoyloxy-2,2,6,6-tetramethylpiperidine-N-oxyl, 4-oxo-2,2,6,6-tetramethylpiperidine-N-oxyl, 2,2,6,6-tetramethylpiperidine-N-oxyl, and other N-oxy-radical-containing compounds; 4-methoxyphenol, 2,2'-methylenebis(4-ethyl-6-tert-butylphenol), 2,6-di-tert-butyl-4-methylphenol, 2,6-di-tert-butyl-N,N-dimethylamino-p-cresol, 2,4-dimethyl-6-tert-butylphenol, 4-tert-butylcatechol, 4,4'-thio-bis(3-methyl-6-tert-butylphenol), 4,4'-butylidene-bis (3-methyl-6-tert-butylphenol), and other phenolic compounds; methoquinone, hydroquinone, 2,5-di-tert-butylhydroquinone, 2,6-di-tert-butylhydroquinone, benzoquinone, and other quinone compounds; cuprous chloride; copper dimethyldithiocarbamate, and other copper dialkyldithiocarbamates; phenothiazine, N,N'-diphenyl-p-phenylenediamine, phenyl-R-naphthylamine, N,N'-di-R-naphthyl-p-phenylenediamine, N-phenyl-N'-isopropyl-p-phenylenediamine and other amino compounds; and 1,4-dihydroxy-2,2,6,6-tetramethylpiperidine, 1-hydroxy-2,2,6,6-tetramethylpiperidine, 4-hydroxy-2,2,6,6-tetramethylpiperidine, and other hydroxylamine compounds. Out of these examples, preferred are 4-hydroxy-2,2,6,6-tetramethylpiperidine-N-oxyl, 4-acetamino-2,2,6,6-tetramethylpiperidine-N-oxyl, 4-benzoyloxy-2,2,6,6-tetramethylpiperidine-N-oxyl, 4-oxo-2,2,6,6-tetramethylpiperidine-N-oxyl, 2,2,6,6-tetramethylpiperidine-N-oxyl, and other N-oxy-radical-containing compounds. Such polymerization inhibitors may be used singly or in any combination of two or more thereof.

The use amount of the polymerization inhibitor(s) is not particularly limited, and is preferably 0.001 parts or more, more preferably 0.002 parts or more by weight for 100 parts by weight of (meth)acrylic acid chloride, and is preferably 5 parts or less, more preferably 0.1 parts or less by weight therefor.

A crude product yielded by the producing method 1, which contains the (meth)acrylic monomer represented by the general formula (1), is usable, as it is, as a raw material when a (meth)acrylic polymer is obtained (when the monomer is polymerized). In order to remove an excess of the raw material or remove a hydrochloride salt or others that are produced as byproducts, the crude product may be washed with a mixed solvent (an aqueous solution and an organic solvent), and purified into the target substance. Examples of the aqueous solution include respective aqueous basic solutions of sodium hydrogencarbonate, potassium hydrogencarbonate, sodium carbonate, potassium carbonate, sodium hydroxide, potassium hydroxide, and ammonia; and an aqueous acidic solution of acetic acid. Examples of the organic solvent include benzene, toluene, xylene, and other aromatic hydrocarbon solvents; and hexane, heptane, octane, and other aliphatic hydrocarbon solvents.

Furthermore, the following may be used to separate the target substance at a high purity by purification: pure water separation, a glass tube oven, distillation, crystallization, gel column chromatography, and others.

The resultant target substance may be identified, using, for example, gas chromatography (GC), liquid chromatography (LC), gas chromatography mass spectrometry (GC-MS), nuclear magnetic resonance spectrometry (NMR), infrared spectroscopy (IR), or a melting-point measuring device.

The method for producing the compound represented by the general formula (2) is not particularly limited. This compound is yielded by, for example, a method including a step of causing metallic lithium to react with a compound represented by the following general formula (3):

[Formula 5]

wherein $R^2$ to $R^4$ independently represent $-CH_3$ or $-CH_2-O-R^5$, wherein at least one of $R^2$ to $R^4$ represents $-CH_2-O-R^5$; $R^5$ represents an alkyl group having 1 to 4 carbon atoms; and X represents a halogen atom to yield a compound represented by the following general formula (4):

[Formula 6]

wherein $R^2$ to $R^4$ independently represent $-CH_3$ or $-CH_2-O-R^5$, wherein at least one of $R^2$ to $R^4$ represents $-CH_2-O-R^5$; $R^5$ represents an alkyl group having 1 to 4 carbon atoms, and then causing the resultant compound represented by the general formula (4) to react further with a compound represented by the following general formula (5):

[Formula 7]

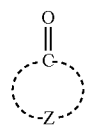

(5)

wherein Z represents multiple atoms necessary for the formation of an alicyclic hydrocarbon group having 3 to 10 carbon atoms in conjunction with a carbon atom (producing method 2).

Examples of the compound represented by the general formula (3) include 2-bromo-1-methoxy-2-methylpropane, 2-bromo-1-ethoxy-2-methylpropane, and 2-bromo-1,3-dimethoxy-2-methyl propane.

Examples of the compound represented by the general formula (5) Include cyclopentanone, cyclohexanone, cycloheptanone, and cyclooctanone.

The producing method 2 is performed preferably under an ordinary pressure and under a gas flow of an inert gas such as argon, or under the atmosphere of an inert gas such as argon.

In the producing method 2, the compound represented by the general formula (3) is caused to react in an amount that is preferably 0.2 moles or more, more preferably 0.4 moles or more per mole of metallic lithium; and that is preferably 1 mole or less, more preferably 0.8 moles or less per mole of the same to heighten the yield of the target substance.

In the producing method 2, the compound represented by the general formula (5) is caused to react in an amount that is preferably 0.4 moles or more, more preferably 0.5 moles or more per mole of the compound represented by the general formula (3), and that is preferably 1.4 moles or less, more preferably 1.2 moles or less per mole of the same to heighten the yield of the target substance.

The reaction temperature in the producing method 2 is preferably −20° C. or higher, more preferably 0° C. or higher, and is preferably 50° C. or lower, more preferably 40° C. or lower to heighten the yield of the target substance.

The reaction period in the producing method 2 is preferably 30 minutes or longer, more preferably 1 hour or longer, and is preferably 12 hours or shorter, more preferably 10 hours or shorter to heighten the yield of the target substance.

In the producing method 2, an organic solvent is preferably used. The organic solvent is not particularly limited, and is preferably an inert organic solvent in the reaction system. Examples of the organic solvent include ether compounds such as tetrahydrofuran and diethyl ether. Such organic solvents may be used singly or in any combination of two or more thereof.

In the producing method 2, the use amount of the organic solvent(s) is not particularly limited, and is usually from about 1 to 100 parts by weight for 100 parts by weight of the total of the raw materials.

A crude product yielded by the producing method 2, which contains the compound represented by the general formula (2), is usable, as it is, as a raw material when the (meth)acrylic monomer represented by the general formula (1) is produced. In order to remove an excess of the raw material, byproducts and others, the crude product may be washed with a mixed solution (an aqueous solution and an organic solvent), and purified into the target substance. Examples of the aqueous solution include respective aqueous basic solutions of sodium hydrogencarbonate, potassium hydrogencarbonate, sodium carbonate, potassium carbonate, sodium hydroxide, potassium hydroxide, and ammonia; and an aqueous acidic solution of acetic acid. Examples of the organic solvent include benzene, toluene, xylene, and other aromatic hydrocarbon solvents; and hexane, heptane, octane, and other aliphatic hydrocarbon solvents.

Furthermore, the following may be used to separate the target substance at a high purity by purification: pure water separation, a glass tube oven, distillation, crystallization, gel column chromatography, and others.

The resultant target substance may be identified, using, for example, gas chromatography (GC), liquid chromatography (LC), gas chromatography mass spectrometry (GC-MS), nuclear magnetic resonance spectrometry (NMR), infrared spectroscopy (IR), or a melting-point measuring device.

EXAMPLES

Hereinafter, the present invention will be described by way of working examples thereof. However, the invention is never limited by these working examples.

Example 1

<Production of Compound Represented by General Formula (2)>

Into a reaction tank equipped with a stirrer, a thermometer and a condenser were charged 0.4 g (58 mmol) of metallic lithium, and 8.0 g of tetrahydrofuran (THF) under an argon atmosphere, and the system was cooled to 10° C. Into 8.0 g of THF were blended 6.55 g (39 mmol) of 2-bromo-1-methoxy-2-methyl-propane and 2 g (24 mmol) of cyclopentanone, and then the mixture was dropwise added into the tank to cause the reactive components to react with each other. After the end of the addition, the reaction liquid was stirred at 15° C. or lower for one hour, and the temperature of the system was raised into a temperature of 20 to 25° C. The reactive components were further caused to react with each other for 8 hours. The reaction liquid was cooled to a temperature of 10 to 30° C., and thereto were added 23.6 g of 20% acetic acid and 45 g of n-hexane to separate the liquid into an organic layer and a water layer. Thereafter, the organic layer was washed with a 5% solution of sodium hydrogencarbonate in water, and next with pure water. The organic layer was then concentrated. The resultant residue was purified through a glass tube oven to yield 0.41 g (2.4 mmol) of 1-(2-methoxy-1,1-dimethyl-ethyl)-cyclopentanol, which is represented by the following general formula (6):

[Formula 8]

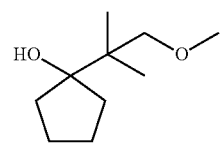

(6)

About 1-(2-methoxy-1,1-dimethyl-ethyl)-cyclopentanol, which is represented by the general formula (6), the structure thereof was identified by $^1$H-NMR measurement (500 MHz, CDCl$_3$) using a JEOL-JNM-ECA500-FT NMR spectrometer manufactured by JEOL Ltd. The resultant NMR spectrum is shown in FIG. 1.

[Assignment of Peaks]
1) 3.28 ppm: methyl group (methyl group in the methoxy group),
2) 3.25 ppm: methylene group, protons (protons in the methylene group adjacent to the ethyl oxygen, and the alcohol),
3) 1.78 to 1.42 ppm: methylene groups (methylene groups in the five-membered ring), and
4) 0.89 ppm: methyl groups (two methyls in the t-Bu group).

<Production of (Meth)Acrylic Monomer Represented by General Formula (1)>

Under a nitrogen atmosphere, into a reaction tank equipped with a stirrer, a thermometer and a condenser were charged 2.87 g (17 mmol) of the compound yielded as described, 1-(2-methoxy-1,1-dimethyl-ethyl)-cyclopentanol, 2.36 g (23 mmol) of triethylamine, and 5.74 g of toluene. Thereto was dropwise added 2.09 g (20 mmol) of methacrylic acid chloride at 20 to 40° C. to cause the reactive components to react with each other. After the end of the addition, the reaction system was stirred for 5 hours, and thereto was added 4.72 g of a 5% sodium hydrogencarbonate solution in water to separate the liquid into an organic layer and an aqueous layer. Thereafter, the organic layer was washed with pure water, and then concentrated. The resultant residue was purified through a glass tube oven to yield 2.40 g (10 mmol) of 1-(2-methoxy-1,1-dimethyl-ethyl)-cyclopentyl methacrylate, which is represented by the following general formula (7):

[Formula 9]

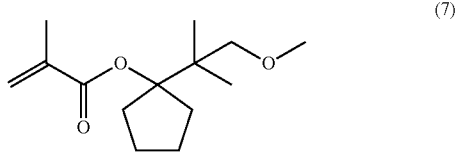

(7)

Figure 2:
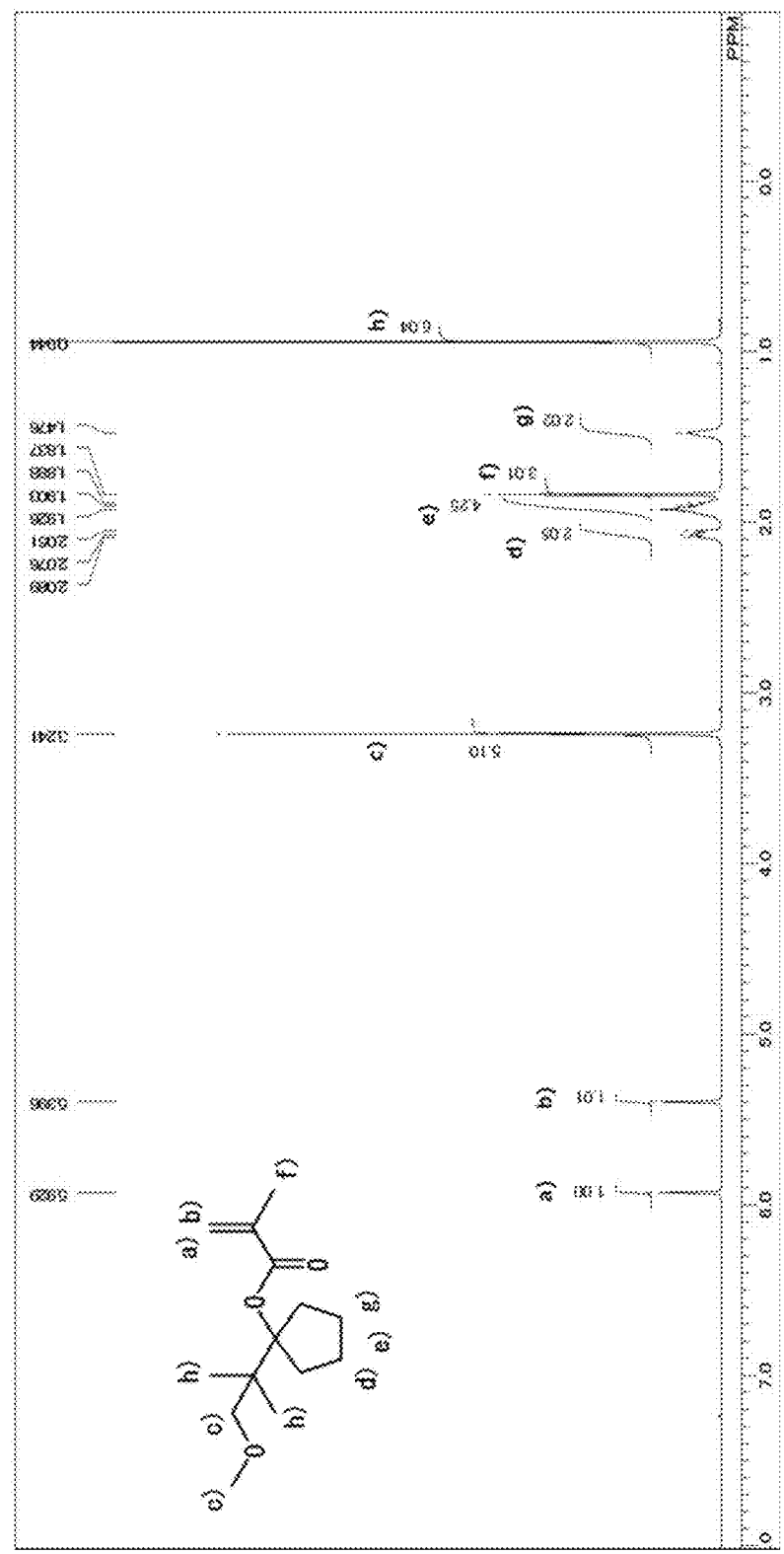
FIG. 2 is an NMR spectrum of the structure of 1-(2-methoxy-1,1-dimethyl-ethyl)-cyclopentyl methacrylate represented by a general formula (7) and yielded in Example 1.

About 1-(2-methoxy-1,1-dimethyl-ethyl)-cyclopentyl methacrylate, which is represented by the general formula (7), the structure thereof was identified by $^1$H-NMR measurement (500 MHz, CDCl$_3$) using a JEOL-JNM-ECA500-FT NMR spectrometer manufactured by JEOL Ltd. The resultant NMR spectrum is shown in FIG. 2.

[Assignment of Peaks]
1) 5.93 ppm and 5.40 ppm: methylene groups (terminated proton moiety of the methacryl group olefin),
2) 3.24 ppm: methyl group and methylene group (methyl and methylene on both sides of the methoxy oxygen),
3) 2.08 ppm, 1.92 ppm and 1.48 ppm: methylene groups (methylene groups in the five-membered ring),
4) 1.84 ppm: methyl group (methyl in the methacryl group), and
5) 0.94 ppm: methyl groups (two methyls in the t-Bu group).

<Evaluation of Eliminability with Acid (Acid Degradability)>

Into a 10 mL sample bottle were charged 0.2 g of the compound yielded as described and represented by the general formula (7), 1-(2-methoxy-1,1-dimethyl-ethyl)-cyclopentyl methacrylate (abbreviated to MEO-TBCPMA), 0.2 g of n-butyl benzene, and 4 g of solution of 1% by weight of a methanesulfonic acid in MEK. The reaction system was stirred with a rotator at room temperature. After 30 minutes, a sample was taken out therefrom, and the remaining percentage of MEO-TBCPMA therein was gained, using liquid chromatography. The result is shown in Table 1.

[Method for Calculating Remaining Percentage]

Remaining percentage (%)=("MEO-TBCPMA area after 30 minutes"/"n-butyl benzene area after 30 minutes")/("MEO-TBCPMA area at initial stage (after zero minutes)"/"n-butyl benzene area at initial stage (after zero minutes)")×100

[LC Measuring Conditions]
Column: CAPCELL PAC C18 ACR S-5 µm,
Eluent: acetonitrile/water=80/20 (ratio by volume)
Flow rate: 1.0 mL/min., and
Detection: absorption at 220 nm.

Example 2

<Production of Compound Represented by General Formula (2)>

Into a reaction tank equipped with a stirrer, a thermometer and a condenser were charged 0.4 g (58 mmol) of metallic lithium, and 8.0 g of tetrahydrofuran (THF) under an argon atmosphere, and the system was cooled to 10° C. Into 8.0 g of THF were blended 7.73 g (39 mmol) of 2-bromo-1,3-dimethoxy-2-methyl-propane and 2 g (24 mmol) of cyclopentanone, and then the mixture was dropwise added into the tank to cause the reactive components to react with each other. After the end of the addition, the reaction liquid was stirred at 15° C. or lower for one hour, and the temperature of the system was raised into a temperature of 20 to 25° C. The reactive components were further caused to react with each other for 8 hours. The reaction liquid was cooled to a temperature of 10 to 30° C., and thereto were added 23.6 g of 20% acetic acid and 45 g of n-hexane to separate the liquid into an organic layer and a water layer. Thereafter, the organic layer was washed with a 5% solution of sodium hydrogencarbonate in water, and next with pure water. The organic layer was then concentrated. The resultant residue was purified through a glass tube oven to yield 0.24 g (1.2 mmol) of 1-(2-methoxy-1-methoxymethyl-1-methyl-ethyl)-cyclopentanol, which is represented by the following general formula (8):

[Formula 10]

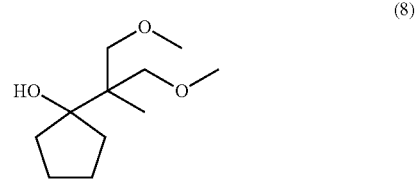

(8)

Figure 3:
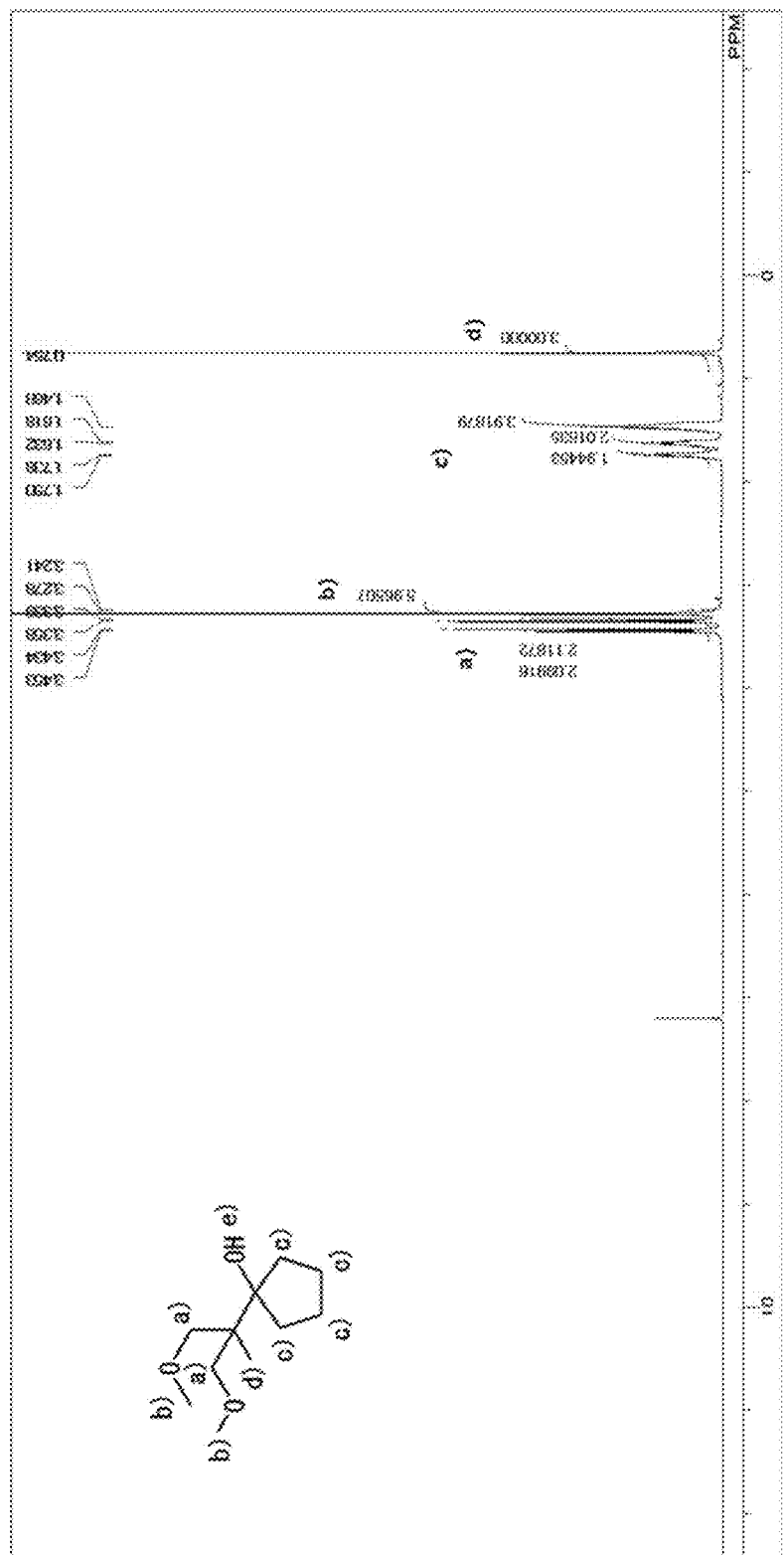
FIG. 3 is an NMR spectrum of 1-(2-methoxy-1-methoxymethyl-1-methyl-ethyl)-cyclopentanol represented by a general formula (8) and yielded in Example 2.

About 1-(2-methoxy-1-methoxymethyl-1-methyl-ethyl)-cyclopentanol, which is represented by the general formula (8), the structure thereof was identified by $^1$H-NMR measurement (500 MHz, CDCl$_3$). The resultant NMR spectrum is shown in FIG. 3.

[Assignment of Peaks]
a) 3.45 ppm, and 3.35 ppm: methylene groups (two methylene groups on both sides of the oxygen atom,
b) 3.28 ppm: methyl group (methyl group in the methoxy group),
c) 1.75 to 1.47 ppm: methylene groups (methylene groups in the five-membered ring),
d) 0.75 ppm: methyl groups (methyls in the t-Bu group), and
e) N.D.: proton in the alcohol.

<Production of (Meth)Acrylic Monomer Represented by General Formula (1)>

Under a nitrogen atmosphere, into a reaction tank equipped with a stirrer, a thermometer and a condenser were charged 1.21 g (6.0 mmol) of the compound yielded as described, 1-(2-methoxy-1-methoxymethyl-1-methyl-ethyl)-cyclopentanol, 4.67 g (46 mmol) of triethylamine, and 2.41 g of toluene. Thereto was dropwise added 3.76 g (36 mmol) of methacrylic acid chloride at 30 to 50° C. to cause the reactive components to react with each other. After the end of the addition, the reaction system was stirred for 24 hours, and thereto was added 12.4 g of a 5% aqueous sodium hydrogencarbonate solution to separate the liquid into an organic layer and an aqueous layer. Thereafter, the organic layer was washed with pure water, and then concentrated. The resultant residue was purified through a glass tube oven to yield 0.36 g (1.3 mmol) of 1-(2-methoxy-1-methoxymethyl-1-methyl-ethyl)-cyclopentyl methacrylate, which is represented by the following general formula (9):

[Formula 11]

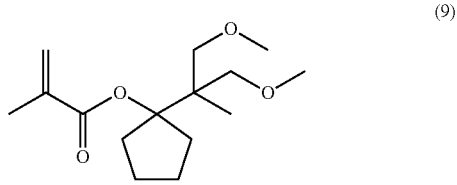

(9)

Figure 4:
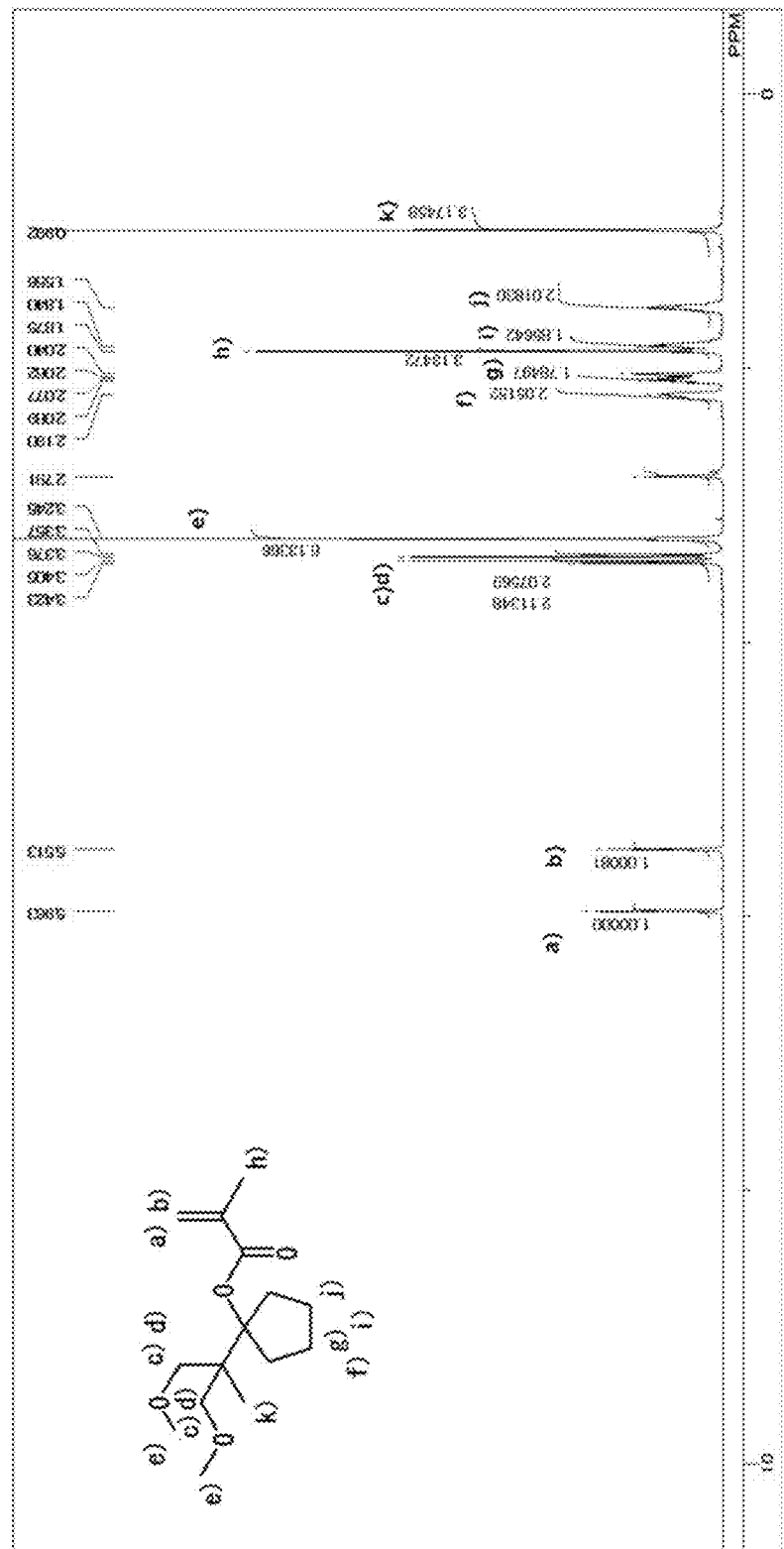
FIG. 4 is an NMR spectrum of the structure of 1-(2-methoxy-1-methoxymethyl-1-methyl-ethyl)-cyclopentyl methacrylate represented by a general formula (9) and yielded in Example 2.

About 1-(2-methoxy-1-methoxymethyl-1-methyl-ethyl)-cyclopentyl methacrylate, which is represented by the general formula (9), the structure thereof was identified by $^1$H-NMR measurement (500 MHz, $CD_3COCD_3$). The resultant NMR spectrum is shown in FIG. 4.

[Assignment of Peaks]
a) and b) 5.96 and 5.51 ppm: olefin terminals,
c) and d) 3.41 and 3.36 ppm: methylene groups (two methylene groups on both sides of the oxygen atom),
e) 3.25 ppm: methyl group (methyl group in the methoxy group),
f), g), i) and j) 2.19, 2.07, 1.86 and 1.56 ppm: methylene groups (methylene groups in the five-membered ring,
h) 1.86 ppm: methyl group (methyl in the methacryl group), and
k) 0.99 ppm: methyl groups (methyls in the t-Bu group).

<Evaluation of Eliminability with Acid (Acid Degradability)>

Into a 10 mL sample bottle were charged 0.2 g of the compound yielded as described and represented by the general formula (9), 1-(2-methoxy-1-methoxymethyl-1-methyl-ethyl)-cyclopentyl methacrylate (abbreviated to MEO2-TBCPMA), 0.2 g of n-butyl benzene, and 4 g of solution of 1% by weight of a methanesulfonic acid in MEK. The reaction system was stirred with a rotator at room temperature. After 30 minutes, a sample was taken out therefrom, and the remaining percentage of MEO2-TBCPMA therein was gained, using liquid chromatography. The result is shown in Table 1.

[Method for Calculating Remaining Percentage]

Remaining percentage (%)=("MEO2-TBCPMA area after 30 minutes"/"n-butyl benzene area after 30 minutes")/("MEO2-TBCPMA area at initial stage (after zero minutes)"/"n-butyl benzene area at initial stage (after zero minutes)")×100

[LC Measuring Conditions]
Column: CAPCELL PAC C18 ACR S-5 μm,
Eluent: acetonitrile/water=65/35 (ratio by volume),
Flow rate: 1.0 mL/min., and
Detection: absorption at 220 nm.

Comparative Examples 1 and 2

<Production of Methacrylic Monomer in Comparative Example 1>

Into a reaction tank equipped with a stirrer, a thermometer and a condenser were charged 0.4 g (58 mmol) of metallic lithium, and 8.0 g of tetrahydrofuran (THF) under an argon atmosphere, and the system was cooled to 10° C. Into 8.0 g of THF were blended 5.97 g (39 mmol) of 2-bromo-2-methoxy-propane and 2 g (24 mmol) of cyclopentanone, and then the mixture was dropwise added into the tank to cause the reactive components to react with each other. After the end of the addition, the reaction liquid was stirred at 15° C. or lower for one hour, and the temperature of the system was raised into a temperature of 20 to 25° C. The reactive components were further caused to react with each other for 8 hours. The reaction liquid was cooled to a temperature of 10 to 30° C., and thereto were added 23.6 g of 20% acetic acid and 45 g of n-hexane to separate the liquid into an organic layer and a water layer. Thereafter, the organic layer was washed with a 5% solution of sodium hydrogencarbonate in water, and next with pure water. The organic layer was then concentrated. The resultant residue was purified through a glass tube oven to yield 0.38 g (2.4 mmol) of 1-(1-methoxy-1-methylethyl)-cyclopentanol.

Under a nitrogen atmosphere, into a reaction tank equipped with a stirrer, a thermometer and a condenser were charged 2.35 g (15 mmol) of the compound yielded as described, 1-(1-methoxy-1-methylethyl)-cyclopentanol, 2.10 g (21 mmol) of triethylamine, and 5.74 g of toluene. Thereto was dropwise added 1.86 g (18 mmol) of methacrylic acid chloride at 20 to 40° C. to cause the reactive components to react with each other. After the end of the addition, the reaction system was stirred for 5 hours, and thereto was added 4.72 g of a 5% sodium hydrogencarbonate solution in water to separate the liquid into an organic layer and an aqueous layer. Thereafter, the organic layer was washed with pure water, and then concentrated. The resultant residue was purified through a glass tube oven to yield 2.02 g (8.9 mmol) of 1-(1-methoxy-1-methylethyl)-cyclopentyl methacrylate (abbreviated to MEO-IPCPMA), which is represented by the following general formula (10):

[Formula 12]

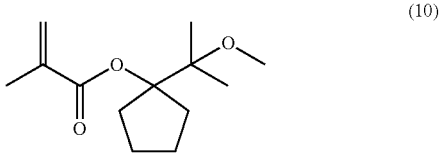

(10)

<Production of Methacrylic Monomer in Comparative Example 2>

The same operations as in the production of the methacrylic monomer in Comparative Example 1 were made except that in the production of the methacrylic monomer in Comparative Example 1, 2-bromo-2-methoxy-propane was changed to 2-bromo-2-methylpropane to yield 1.87 g (8.9 mmol) of 1-t-butyl-cyclopentyl methacrylate (abbreviated to TBCPMA), which is represented by the following general formula (11):

[Formula 13]

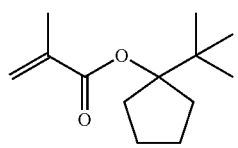
(11)

<Evaluation of Eliminability with Acid (Acid Degradability)>

The same evaluation as in "Evaluation of Eliminability with Acid (Acid Degradability)" was made except that MEO-TBCPMA in Example 1 was changed to each of the methacrylic monomers, which has a structure in Table 1.

TABLE 1

| | Compound name | Structure | Evaluation of eliminability with acid: remaining percentage (%) |
|---|---|---|---|
| Example 1 | 1-(2-Methoxy-1,1-dimethyl-ethyl)-cyclopentyl methacrylate MEO-TBCPMA | 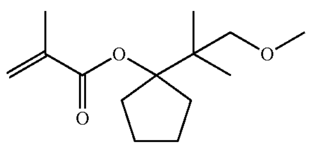 [SMILES: C=C(C)C(=O)OC1(C(C)(C)COC)CCCC1] | 43.8 |
| Example 2 | 1-(2-Methoxy-1-methoxymethyl)-1-methyl-ethyl)-cyclopentyl methacrylate MEO2-TBCPMA | 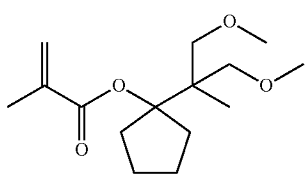 [SMILES: C=C(C)C(=O)OC1(C(C)(COC)COC)CCCC1] | 0.61 |
| Comparative Example 1 | MEO-TPCPMA | 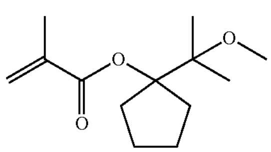 [SMILES: C=C(C)C(=O)OC1(C(C)(C)OC)CCCC1] | 100 |
| Comparative Example 2 | TBCPMA | 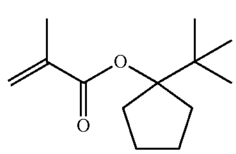 | 73.5 |

It is understood from results in Table 1 that MEO-TBCPMA yielded in Example 1 and MEO2-TBCPMA yielded in Example 2 have a higher eliminability with acid (high acid-degradability) than the respective methacrylic monomers used in Comparative Examples 1 and 2, which each have a tertiary cycloalkyl group.

What is claimed is:

1. A (meth)acrylic monomer represented by general formula (1):

[Formula 1]

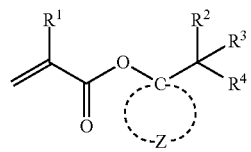
(1)

wherein $R^1$ represents a hydrogen atom or a methyl group; $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

2. The (meth)acrylic monomer according to claim 1, wherein the alicyclic hydrocarbon group is a monocyclic alicyclic hydrocarbon group or monocyclic alicyclic hydrocarbon group having a substituent, a condensed alicyclic hydrocarbon group or condensed alicyclic hydrocarbon group having a substituent, an adamantyl group or adamantyl group having a substituent, a dicyclopentanyl group or dicyclopentanyl group having a substituent, or an isobornyl group or isobornyl group having a substituent.

3. The (meth)acrylic monomer according to claim 2, wherein the monocyclic alicyclic hydrocarbon group is cyclopentane, cyclohexane, cycloheptane, or cyclooctane.

4. A compound represented by general formula (2):

[Formula 2]

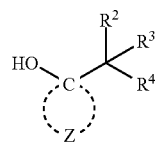

(2)

wherein $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

5. A method for producing the (meth)acrylic monomer recited in claim 1, comprising a step of causing (meth)acrylic acid chloride to react with a compound represented by general formula (2):

[Formula 2]

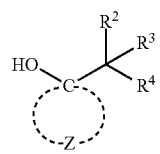

(2)

wherein $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

6. A method for producing the (meth)acrylic monomer recited in claim 2, comprising a step of causing (meth)acrylic acid chloride to react with a compound represented by general formula (2):

[Formula 2]

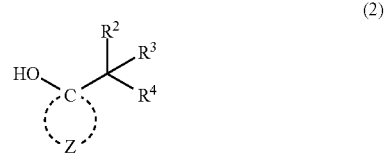

(2)

wherein $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

7. A method for producing the (meth)acrylic monomer recited in claim 3, comprising a step of causing (meth)acrylic acid chloride to react with a compound represented by general formula (2):

[Formula 2]

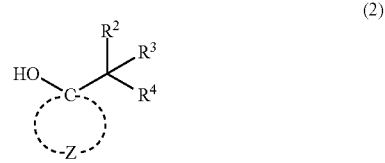

(2)

wherein $R^2$ to $R^4$ independently represent —$CH_3$ or —$CH_2$—O—$R^5$, wherein at least one of $R^2$ to $R^4$ represents —$CH_2$—O—$R^5$; $R^5$ represents an alkyl group having 1 to 4 carbon atoms; and Z represents multiple atoms necessary for the formation of an alicyclic hydrocarbon group having 3 to 10 carbon atoms in conjunction with a carbon atom.

* * * * *